United States Patent
Drake et al.

(10) Patent No.: US 11,090,081 B2
(45) Date of Patent: Aug. 17, 2021

(54) EXTRAVASCULAR MEDICAL ACCESS TOOLS HAVING BORING TIP AND METHODS OF USING SUCH TOOLS

(71) Applicant: Medtronic, Inc., Minneapolis, MN (US)

(72) Inventors: Ronald A. Drake, St. Louis Park, MN (US); Lester O. Stener, Hudson, WI (US); John A. Lange, Inver Grove Heights, MN (US); Mitchell R. Maciver, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 168 days.

(21) Appl. No.: 16/362,740

(22) Filed: Mar. 25, 2019

(65) Prior Publication Data

US 2019/0216502 A1 Jul. 18, 2019

Related U.S. Application Data

(62) Division of application No. 15/139,546, filed on Apr. 27, 2016, now Pat. No. 10,245,072.

(60) Provisional application No. 62/190,891, filed on Jul. 10, 2015.

(51) Int. Cl.
*A61B 17/16* (2006.01)
*A61B 17/34* (2006.01)
*A61N 1/05* (2006.01)
*A61B 17/32* (2006.01)
(Continued)

(52) U.S. Cl.
CPC ...... *A61B 17/3468* (2013.01); *A61B 17/1691* (2013.01); *A61B 17/32002* (2013.01); *A61N 1/05* (2013.01); *A61N 1/0504* (2013.01); *A61B 18/14* (2013.01); *A61B 2017/0046* (2013.01); *A61B 2017/00243* (2013.01);
(Continued)

(58) Field of Classification Search
CPC ........ A61B 17/1691; A61B 2017/0046; A61B 2017/00469
See application file for complete search history.

(56) References Cited

U.S. PATENT DOCUMENTS

| | | |
|---|---|---|
| 2,114,695 A | 4/1938 | Anderson |
| 3,835,864 A | 9/1974 | Rasor et al. |
| 4,655,219 A | 4/1987 | Petruzzi |

(Continued)

FOREIGN PATENT DOCUMENTS

EP 2204127 A1 7/2010

OTHER PUBLICATIONS

Medtronic, Inc. 6996T Tunneling Tool, Technical Manual, 12 pages.
(Continued)

*Primary Examiner* — Melanie R Tyson
(74) *Attorney, Agent, or Firm* — Shumaker & Sieffert, P.A.

(57) ABSTRACT

A detachable handle assembly for a tool, the tool for creating a sub-sternal tunnel in a patient. The handle assembly includes a lock-and-release mechanism by which the tunneling assembly is attached to the handle, the mechanism being operable to detach the handle from the tunneling assembly. The handle assembly also may include a knob that interlocks with the tunneling assembly, the knob being configured for engagement by fingers of an adult hand to apply a force to rotate a boring tip of the tunneling assembly.

13 Claims, 11 Drawing Sheets

(51) Int. Cl.
*A61B 18/14* (2006.01)
*A61B 17/00* (2006.01)

(52) U.S. Cl.
CPC ............. *A61B 2017/320044* (2013.01); *A61B 2017/320056* (2013.01)

(56) References Cited

U.S. PATENT DOCUMENTS

| | | |
|---|---|---|
| 4,687,471 A | 8/1987 | Twardowski et al. |
| 4,710,181 A | 12/1987 | Fuqua |
| 5,026,377 A | 6/1991 | Burton et al. |
| 5,171,233 A | 12/1992 | Amplatz et al. |
| 5,234,437 A | 8/1993 | Sepetka |
| 5,350,397 A | 9/1994 | Palermo et al. |
| 5,417,697 A | 5/1995 | Wilk et al. |
| 5,476,510 A | 12/1995 | Eberhardt et al. |
| 5,632,755 A | 5/1997 | Nordgren et al. |
| 6,156,055 A | 12/2000 | Ravenscroft |
| 6,187,016 B1 | 2/2001 | Hedges et al. |
| 6,277,125 B1 | 8/2001 | Barry et al. |
| 6,348,056 B1 | 2/2002 | Bates et al. |
| 6,355,060 B1 | 3/2002 | Lenker et al. |
| 6,501,993 B2 | 12/2002 | Morgan et al. |
| 6,506,205 B2 | 1/2003 | Goldberg et al. |
| 6,846,317 B1 | 1/2005 | Nigon |
| 6,953,473 B2 | 10/2005 | Porter |
| 7,033,376 B2 | 4/2006 | Tsukernik |
| 7,323,003 B2 | 1/2008 | Lowe |
| 8,025,668 B2 | 9/2011 | McCartney |
| 8,364,280 B2 | 1/2013 | Marnfeldt et al. |
| 8,574,192 B2 | 11/2013 | Haarala et al. |
| 8,777,932 B2 | 7/2014 | Sage et al. |
| 8,945,145 B2 | 2/2015 | Tran et al. |
| 9,237,948 B2 | 1/2016 | Colson et al. |
| 9,480,850 B2 | 11/2016 | Schmidt et al. |
| 9,700,732 B2 | 7/2017 | Schmidt et al. |
| 9,775,636 B2 | 10/2017 | Fazio et al. |
| 9,844,664 B2 | 12/2017 | McEvoy et al. |
| 10,004,467 B2 | 6/2018 | Lahm et al. |
| 2004/0102804 A1 | 5/2004 | Chin |
| 2005/0159771 A1 | 7/2005 | Petersen |
| 2006/0015130 A1 | 1/2006 | Voorhees et al. |
| 2006/0085041 A1 | 4/2006 | Hastings et al. |
| 2006/0247572 A1 | 11/2006 | McCartney |
| 2007/0005131 A1 | 1/2007 | Taylor |
| 2008/0065011 A1 | 3/2008 | Marchand et al. |
| 2009/0182370 A1 | 7/2009 | Volobuyev et al. |
| 2012/0083794 A1 | 4/2012 | Martin et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0184987 A1 | 7/2012 | Sirota |
| 2012/0239130 A1 | 9/2012 | Hartley et al. |
| 2013/0053921 A1 | 2/2013 | Bonner et al. |
| 2013/0103047 A1 | 4/2013 | Steingisser et al. |
| 2013/0131591 A1 | 5/2013 | Berthiaume et al. |
| 2013/0253480 A1* | 9/2013 | Kimball ......... A61B 17/320092 606/1 |
| 2013/0310869 A1 | 11/2013 | Crenshaw et al. |
| 2014/0142621 A1 | 5/2014 | Masters et al. |
| 2014/0163579 A1 | 6/2014 | Tischendorf et al. |
| 2014/0330208 A1 | 11/2014 | Christie et al. |
| 2014/0330248 A1 | 11/2014 | Thompson-Nauman et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0094668 A1 | 4/2015 | Wood et al. |
| 2015/0094735 A1 | 4/2015 | Ward et al. |
| 2015/0105793 A1 | 4/2015 | Cole |
| 2015/0133952 A1 | 5/2015 | Seifert et al. |
| 2015/0133953 A1 | 5/2015 | Seifert et al. |
| 2015/0209077 A1 | 7/2015 | Marshall |
| 2015/0273212 A1 | 10/2015 | Berthiaume et al. |
| 2015/0305695 A1 | 10/2015 | Lahm et al. |
| 2015/0306375 A1 | 10/2015 | Marshall et al. |
| 2015/0306410 A1 | 10/2015 | Marshall et al. |
| 2016/0015968 A1 | 1/2016 | Bonner et al. |
| 2016/0015983 A1 | 1/2016 | Sheldon et al. |
| 2016/0143661 A1 | 5/2016 | Wood et al. |
| 2016/0158567 A1 | 6/2016 | Marshall et al. |
| 2016/0243355 A1 | 8/2016 | Wood |
| 2017/0028190 A1 | 2/2017 | Kealan |
| 2017/0100582 A1 | 4/2017 | McEvoy et al. |

OTHER PUBLICATIONS

Spine Surgical Innovation Catalog, 2011; 52 pages.
NOVA® Optional Accessories (1 page), accessed Nov. 16, 2015, http://www.panamericantool.com/9-32-40-aircraft-collets.html.
(PCT/US2016/041091) PCT Notification of Transmittal of the International Search Report and the Written Opinion of the International Searching Authority, dated Sep. 21, 2016, 11 pages.

* cited by examiner

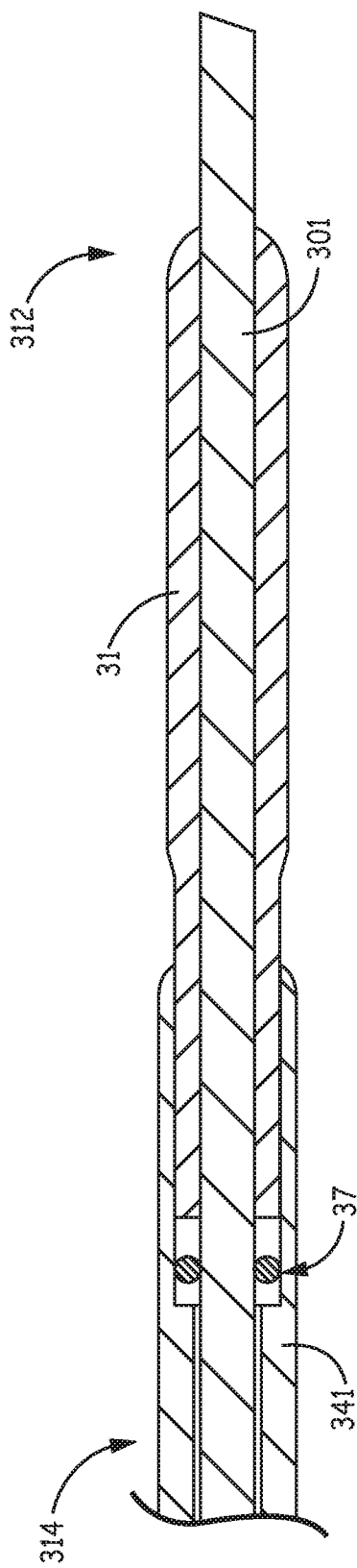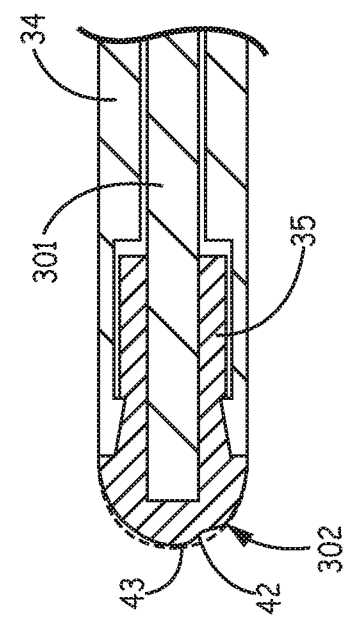

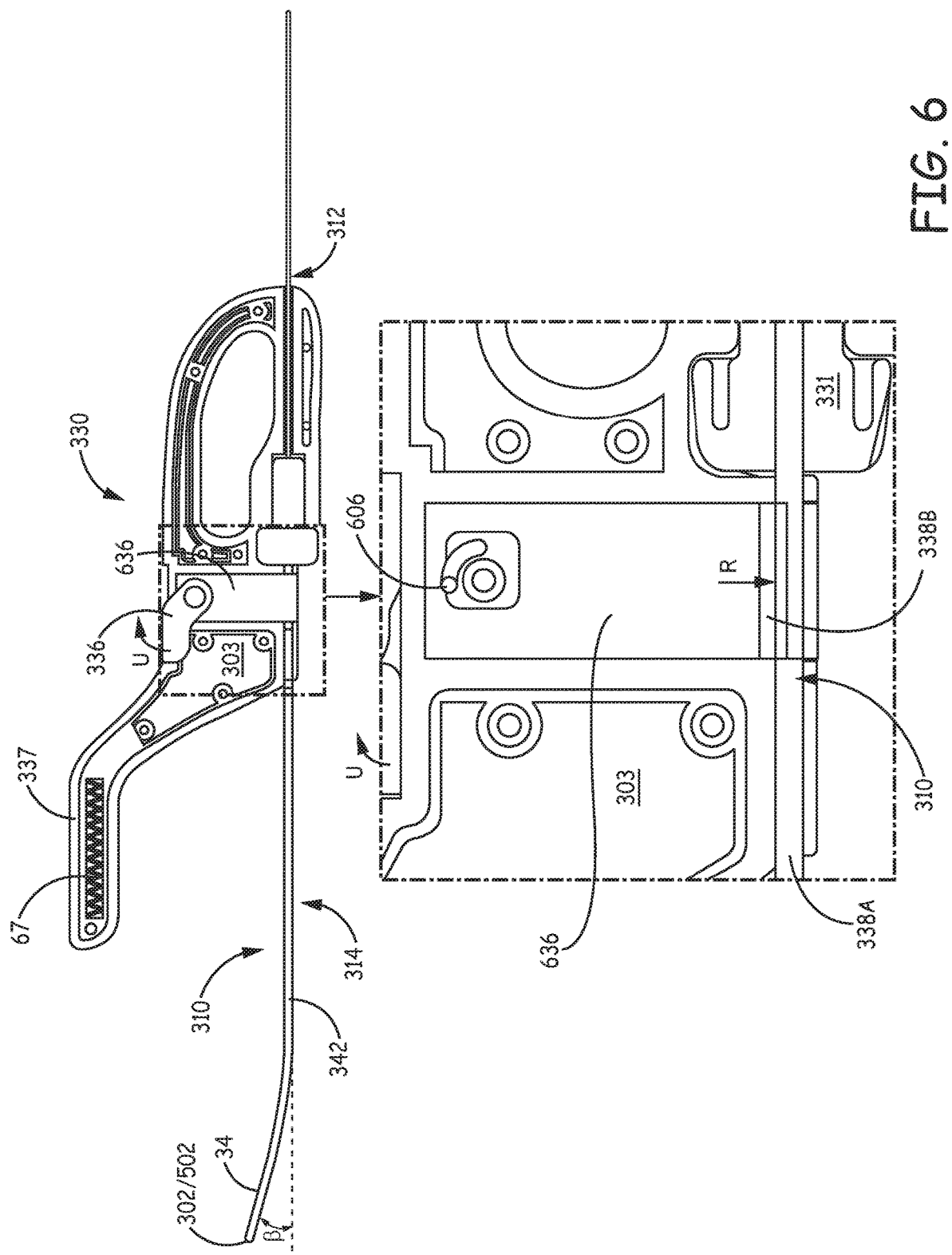

EXTRAVASCULAR MEDICAL ACCESS TOOLS HAVING BORING TIP AND METHODS OF USING SUCH TOOLS

CROSS REFERENCE TO RELATED APPLICATIONS

This application is a Division of U.S. patent application Ser. No. 15/139,546, entitled "EXTRAVASCULAR MEDICAL ACCESS TOOLS HAVING BORING TIP AND METHODS OF USING SUCH TOOLS," filed Apr. 27, 2016 which claims the benefit of the filing date of provisional U.S. Patent Application No. 62/190,891, entitled "EXTRAVASCULAR MEDICAL ACCESS TOOLS HAVING BORING TIP AND METHODS OF USING SUCH TOOLS," filed Jul. 10, 2015, the content of both of which is incorporated by reference in their entirety.

TECHNICAL FIELD

The present disclosure pertains to gaining access to extravascular spaces, and more particularly to tools and associated methods suitable for gaining access into a sub-sternal space for the positioning of a medical device therein.

BACKGROUND

Implantable medical electrical leads, included in systems that are known in the art for delivering cardiac therapy and/or for providing cardiac monitoring, are often implanted transvenously within a heart of a patient. But extravascular implant sites may be preferred, for example, in those patients where vascular access is difficult, or because transvenous leads can become fibrosed in the heart over time, which makes lead revision and extraction procedures challenging.

SUMMARY

This disclosure describes various examples of tools and associated methods suitable for gaining access to extravascular spaces. In one example, this disclosure provides a tool for creating a sub-sternal tunnel in a patient. The tool comprises a handle and a tunneling assembly. The tunneling assembly comprises a relatively rigid tubular member including a proximal portion and a distal portion, the proximal portion being attached to the handle such that the distal portion extends distally from the handle and an elongate inner member extending within the tubular member. The elongate inner member comprises a proximal portion protruding out from the proximal portion of the tubular member and being attached to the handle, the proximal portion of the inner member including an interface for receiving a force that rotates the inner member relative to the tubular member and a boring tip without any sharp edge, the tip protruding out from the distal portion of the tubular member and generally conforming to a dome shape but including at least one surface recessed from the dome shape, each of the at least one surface being offset from a summit of the dome shape, the summit of the dome shape coinciding with a distal-most edge of the boring tip.

In another example, this disclosure is directed to a method for positioning a medical device beneath a sternum of a patient. The method comprises positioning a boring tip of a tunneling assembly against diaphragmatic attachments in proximity to the patient's xiphoid process, the tunneling assembly comprising a relatively rigid tubular member, and an elongate inner member extending within the outer tubular member from a proximal portion thereof to the boring tip, a proximal portion of each of the tubular and inner members being attached to a handle such that a distal portion of the tubular member extends distally from the handle, and the boring tip of the inner member protrudes out from the distal portion of the tubular member; causing a rotation of the positioned boring tip, while pushing the tunneling assembly in a superior direction to cross through the diaphragmatic attachments, the rotation being actuated by a hand that grasps the tunneling tool handle; stopping the rotation of the tunneling assembly boring tip after crossing through the diaphragmatic attachments; advancing the tunneling assembly beneath the patient's sternum to create a tunnel, after crossing through the diaphragmatic attachments, and without causing any rotation of the tunneling assembly boring tip; and positioning a medical device within the tunnel.

In a further example, this disclosure is directed to a detachable handle assembly for a tool, the tool for creating a sub-sternal tunnel in a patient, and the handle assembly comprising a lock-and-release mechanism by which the tunneling assembly is attached to the handle, the mechanism being operable to detach the handle from the tunneling assembly; and a knob that interlocks with the tunneling assembly, the knob being configured for engagement by fingers of an adult hand to apply a force to rotate a boring tip of the tunneling assembly.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF THE DRAWINGS

FIG. 3C is a cross-section of a portion of the tunnel assembly of FIG. 3B

FIG. 3D further illustrates an example boring tip of the tunneling assembly of the tool of FIGS. 3A-C.

FIG. 6 is a plan view of the example tool of FIG. 3A with a portion of a shell of the tool handle removed.

DETAILED DESCRIPTION

The following detailed description is exemplary in nature and is not intended to limit, in any way, the scope, applicability, or configuration of the claimed tools and methods. Rather, the following description provides practical examples, and those skilled in the art will recognize that some of the examples may have suitable alternatives.

Figure 1A:
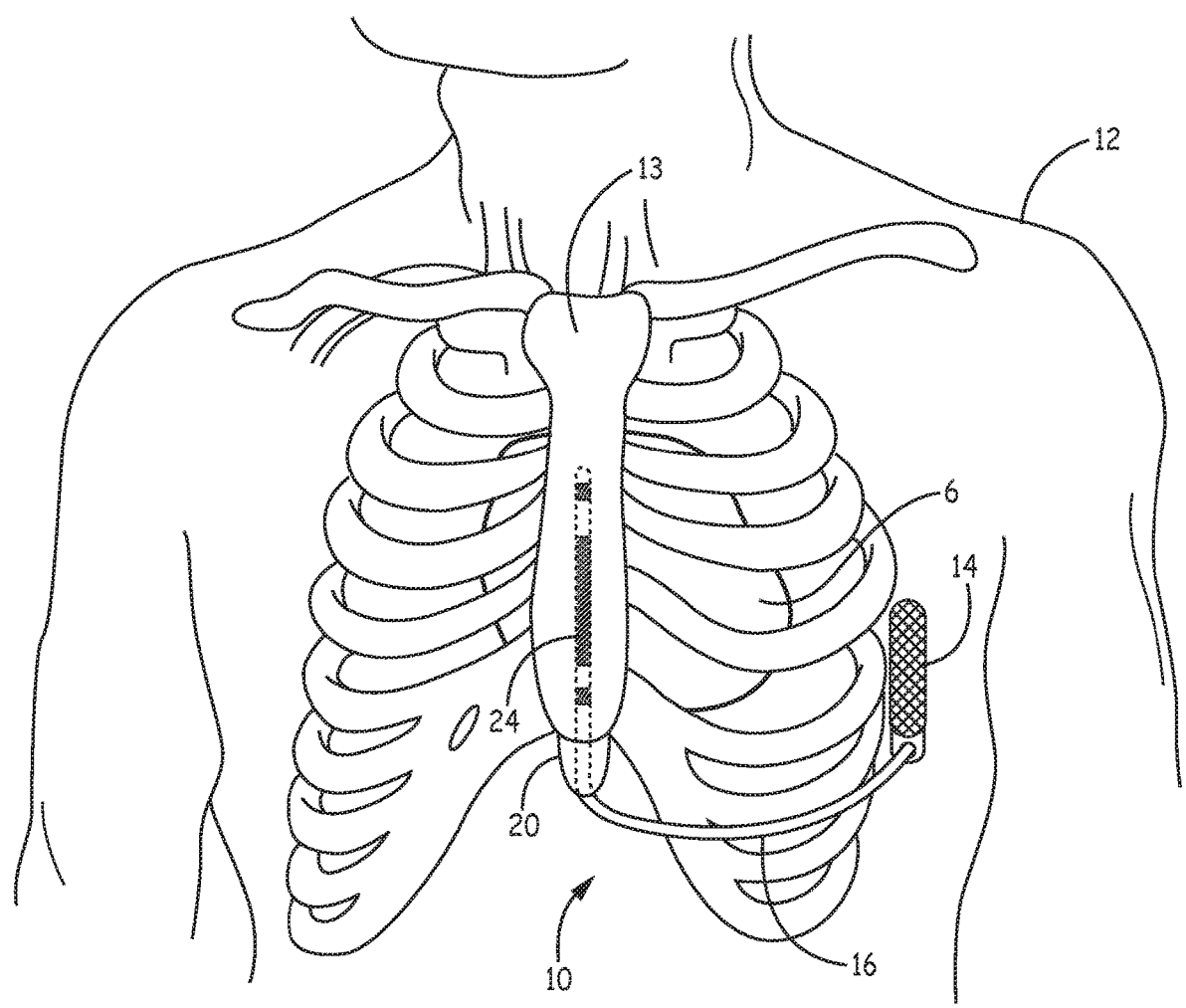
FIGS. 1A-B are schematics showing an exemplary extravascular implant of an exemplary system that includes an implantable pulse generator and an implantable medical electrical lead coupled thereto.
Figure 1B:
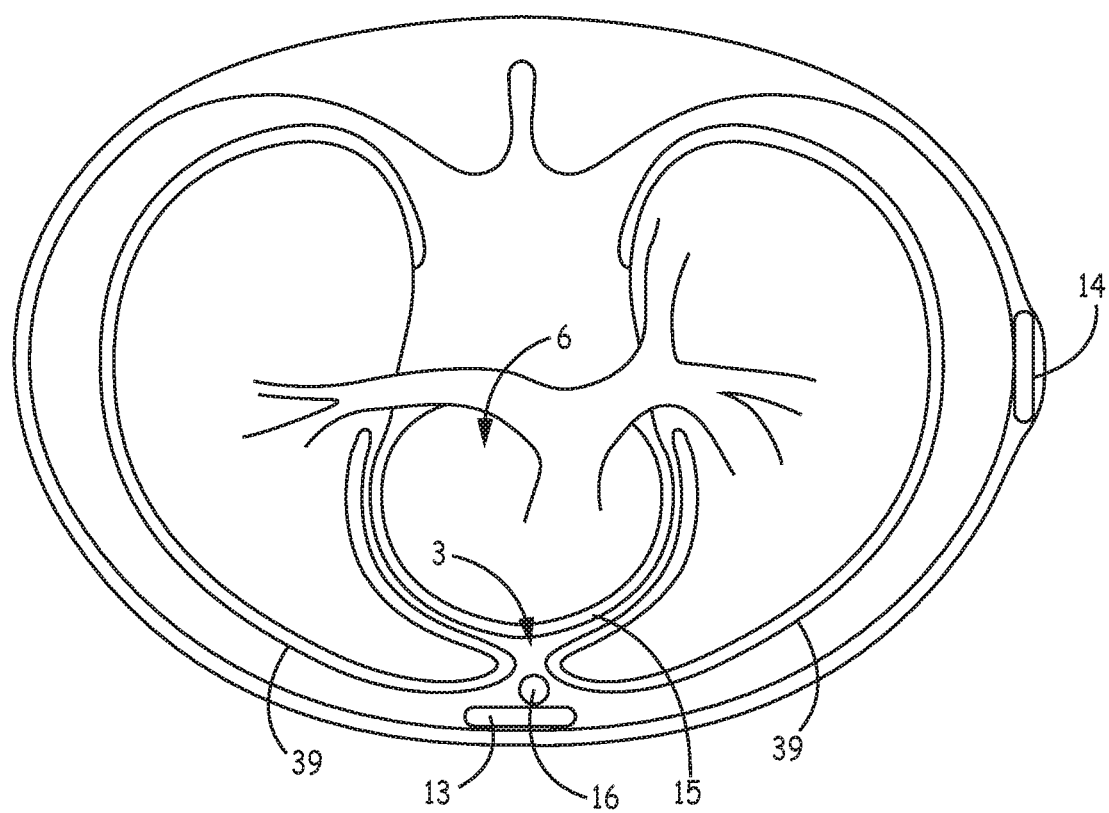

FIGS. 1A-B are schematics showing an exemplary extravascular implant of an exemplary system 10 that includes an implantable pulse generator 14 and an implantable medical electrical lead 16 coupled thereto. Pulse generator 14 is shown implanted subcutaneously on the left mid-axillary of a patient 12, superficially of the patient's ribcage. Pulse generator 14 is configured to provide stimulation on therapy (e.g., defibrillation, cardioversion, and/or pacing). Pulse generator 14 may include a hermetically sealed housing in which the appropriate electronics and a power supply are contained. The housing is formed from a conductive material, such as titanium, or from a combination of conductive and non-conductive materials. Pulse generator 14 further includes a connector module by which lead 16 is electrically coupled to the electronics contained therein, for example, by electrical contacts contained within the module and a corresponding hermetically sealed feedthrough assembly, such as is known in the art. The conductive material of the device housing may be employed as an electrode, for example, to provide the aforementioned therapy in conjunction with a defibrillation electrode 24 of lead 16 or one or more pace/sense electrodes of lead 16.

A proximal portion of lead 16 is shown extending medially from pulse generator 14 toward a sternum 13 of the patient, for example, within a subcutaneous or submuscular tunnel above the ribcage, and a distal portion of lead 16 is shown extending in a superior direction adjacent to the sternum 13, for example within a tunnel formed in a sub-sternal space 3 (e.g., the loose connective tissue and/or sub-sternal musculature of the anterior mediastinum), wherein lead 16 bends in proximity to a xiphoid process 20 of sternum 13, to extend from the subcutaneous tunnel to the sub-sternal tunnel. With reference to FIG. 1B, the sub-sternal space 3 may be viewed as being bounded laterally by pleurae 39 that enclose the patient's lungs, posteriorly by the pericardial sac 15 that encloses the patient's heart 6, and anteriorly by the sternum 13. In some instances, the anterior wall of the anterior mediastinum 3 may also be formed by the transversus thoracis and one or more costal cartilages.

Figure 2:
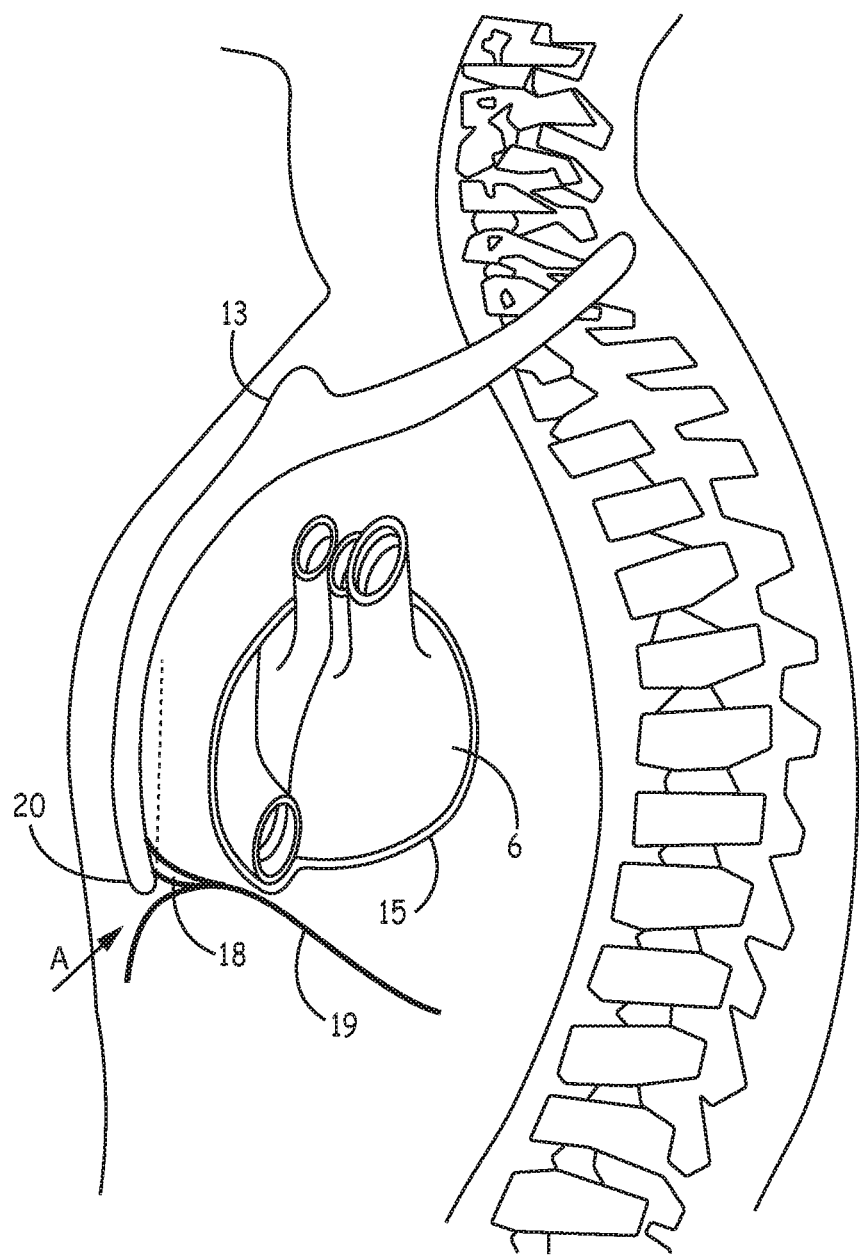
FIG. 2 is a schematic showing an access site for making a passageway between a patient's diaphragm and xiphoid process of sternum, for example, to create a sub-sternal tunnel in which to position a medical device, such as medical electrical lead.

FIG. 2 is a schematic showing an access site A for making a passageway between a patient's diaphragm 19 and xiphoid process 20 of sternum 13, for example, to create a sub-sternal tunnel in which to position a medical device, such as medical electrical lead 16. After making a superficial incision, an operator, using tools and techniques known to those skilled in the art, may open a passageway between diaphragmatic attachments 18 and diaphragm 19, for example, by blunt dissection, in which the operator may employ a tunneling tool, for example, the Medtronic® Model 6996T, to both create the passageway and then form a sub-sternal tunnel (e.g. along the dotted line of FIG. 2). In some cases, a relatively substantial force is necessary to push the blunt tip of the tunneling tool through diaphragmatic attachments 18 such that, once the tip crosses attachments 18, a resulting forward momentum of the tip is difficult to control. Employing a sharp tip can minimize the force necessary to cross diaphragmatic attachments, but such a tip, once across, increases the risk for injuring the heart 6, and/or the pleurae 39, or other structures within the anterior mediastinum 3, such as lymph vessels, lymph glands, branches of the internal thoracic artery, the internal thoracic vein, etc. Embodiments of tools described herein enable an operator to cross diaphragmatic attachments 18 in a controlled fashion, and to subsequently create a sub-sternal tunnel in which to position a medical device, without increasing the risk of subsequent injury to a patient's circulatory and/or respiratory system.

Figure 3A:
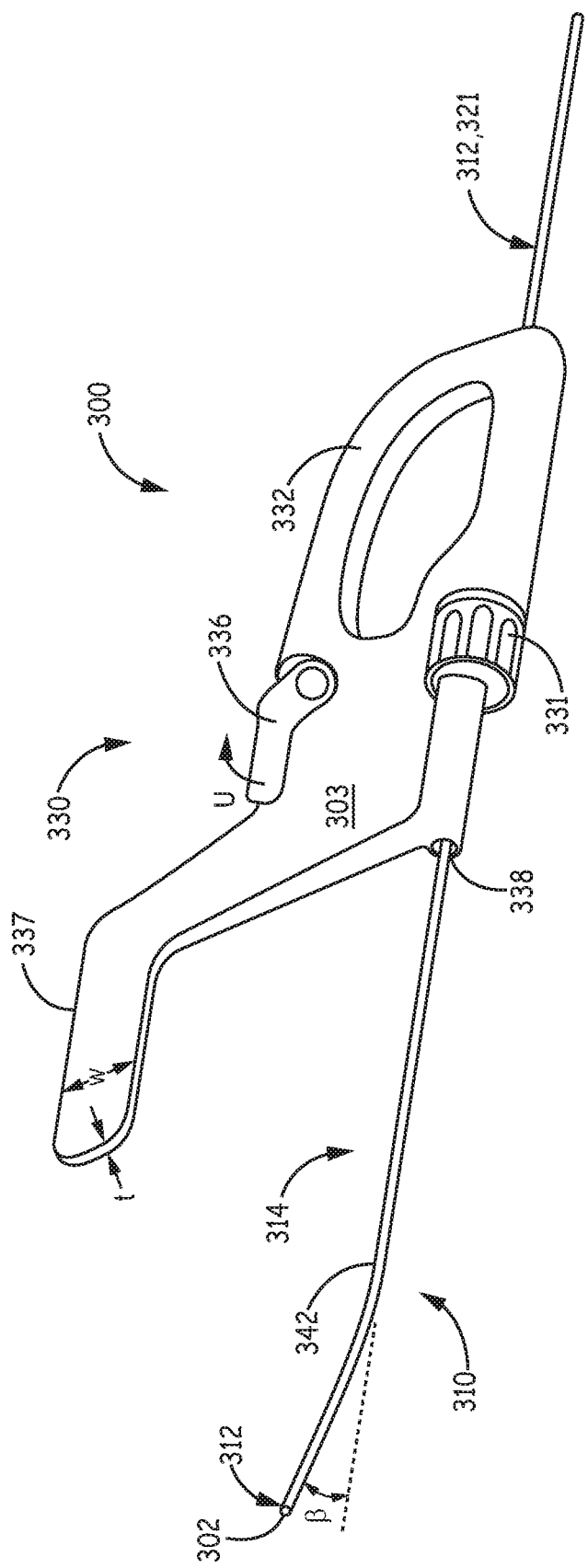
FIG. 3A is a perspective view of an example tool for gaining sub-sternal access and creating a sub-sternal tunnel in a patient
Figure 3B:
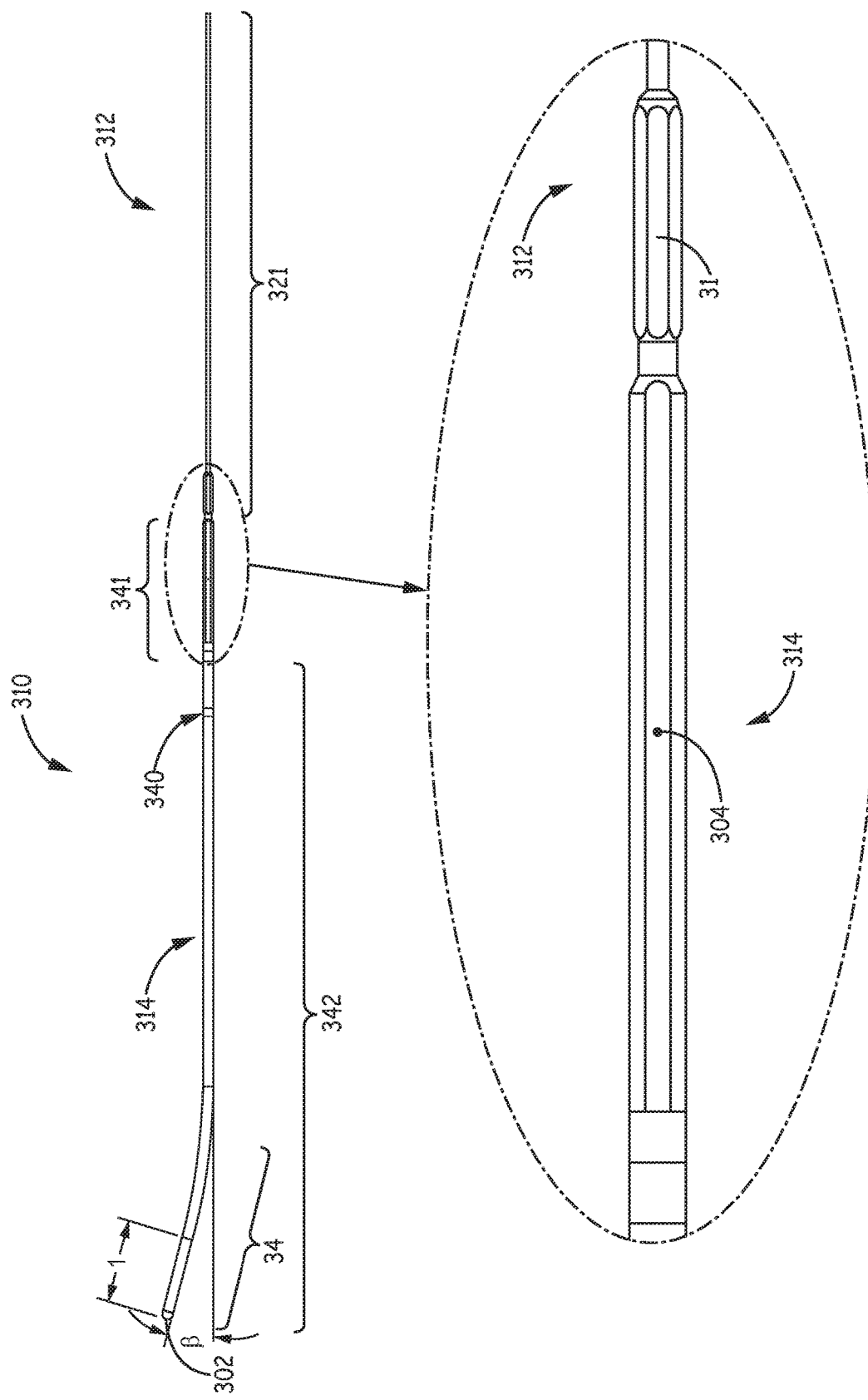
FIG. 3B is a plan view of the tunneling assembly of the example tool of FIG. 3A separated from the handle of the tool.

FIG. 3A is a perspective view of a tool 300 for gaining sub-sternal access and creating a sub-sternal tunnel in a patient, according to some embodiments. Tool 300 is shown including a tunneling assembly 310 and a handle 330 attached thereto. FIG. 3B is a plan view of tunneling assembly 310 separate from handle 330. FIGS. 3A-B illustrate a relatively rigid tubular member 314 and an elongate inner member 312 of tunneling assembly 310, wherein inner member 312 extends within tubular member 314, from a proximal portion 321 thereof to a boring tip 302 thereof. Tubular member includes a proximal portion 341 and a distal portion 342 that extends distally from handle 330. Proximal portion 321 of inner member 312 is shown protruding out from proximal portion 341 of tubular member 314, and boring tip 302 of inner member 312 is shown protruding out from distal portion 342 of tubular member 314. Although FIG. 3A shows inner member proximal portion 321 extending over a length that protrudes proximally from handle 330, proximal portion 321 need not do so, according to some alternate embodiments. Tubular member 314 may have an outer diameter between approximately 0.1 inch (2.5 mm) and approximately 0.14 inch (3.5 mm), for example, approximately 0.125 inch (3.2 mm). One or both of tubular member 314 and inner member 312 are preferably radiopaque for fluoroscopic monitoring during a tunneling procedure, for example, being formed from a medical grade, 300 series stainless steel. According to some alternate embodiments, inner member 312 may be formed from a medical grade polymer, examples of which include, without limitation Polyamide, polycarbonate, high density polyethylene, Polyether ether ketone (PEEK), Acrylonitrile butadiene styrene (ABS), and Polyetherimide (PEI Ultem™)

Figure 7A:
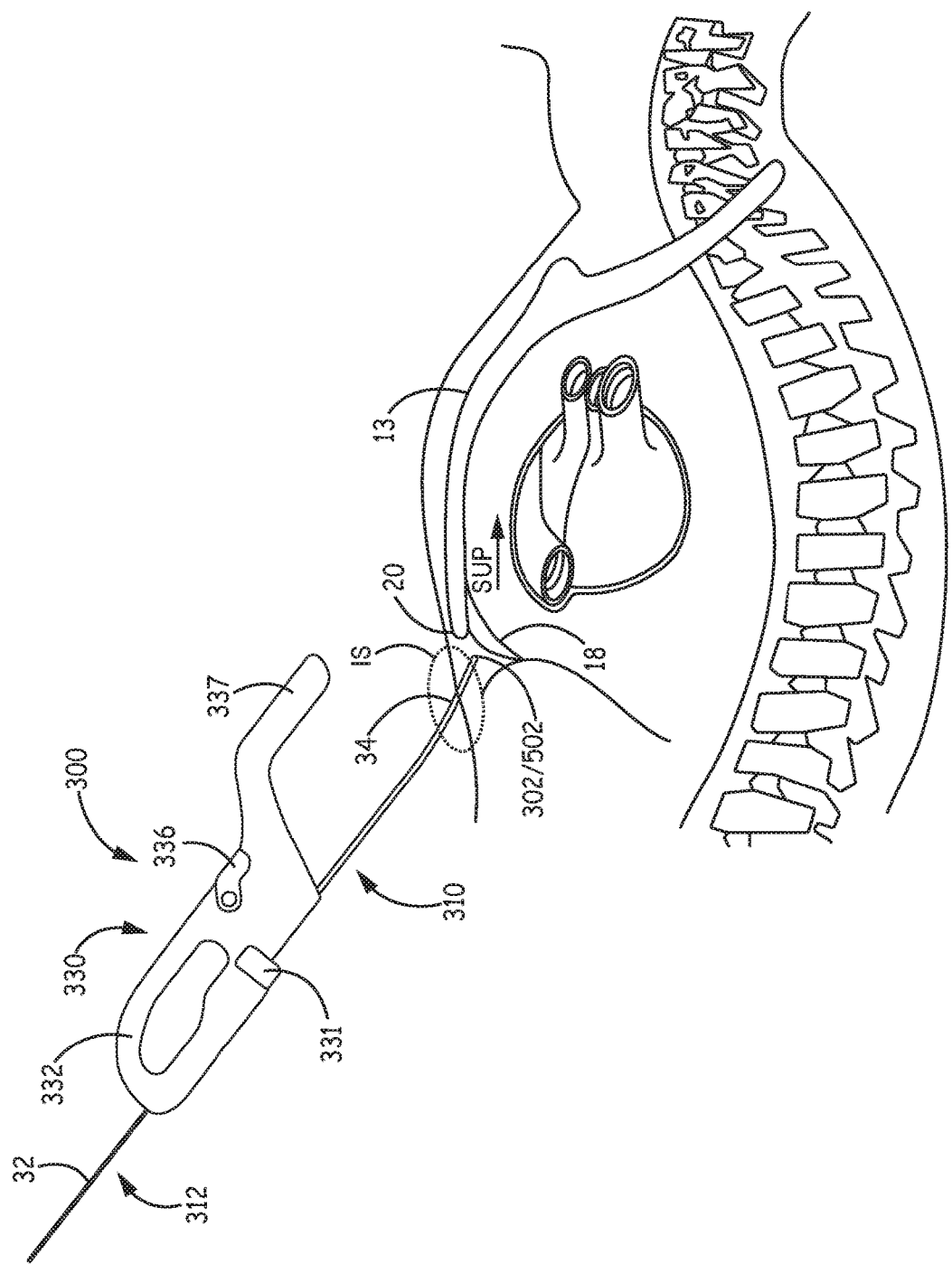
FIG. 7A is a schematic showing the example tool of FIGS. 3A and 6 with tunneling assembly the boring tip having been passed through an incision site IS and positioned against diaphragmatic attachments, in proximity to xiphoid process.

FIG. 3A further illustrates handle 330 including a knob 331 and looped gripping portion 332 extending laterally from knob 331. Gripping portion 332 may be formed integrally with a shell 303 of handle 330, for example, from ABS or polycarbonate, and knob 331 may be formed from ABS. According to the illustrated embodiment, tubular member proximal portion 341 and inner member proximal portion 321 extend within a channel 338 of handle 330, for attachment thereto. Inner member proximal portion 321 includes an interface 31 for receiving a force that rotates inner member 312 relative to tubular member 314, thereby driving boring tip 302 of inner member 312 to aid in crossing diaphragmatic attachments 18 (FIGS. 2 and 7A). The force that rotates inner member 312 may be applied by an operator's fore-finger and thumb that engage with knob 331, for example, when the operator's hand grips around looped gripping portion 332 of handle 330. It should be noted that, in some alternate embodiments, knob 331 may be replaced by another suitable operator interface, for example, a trigger.

With reference to the enlarged detail of FIG. 3B and the corresponding longitudinal cross-section of FIG. 3C, inner member interface 31, according to some exemplary embodiments, is formed by a separate component, which is fitted around, and coupled to a shaft component 301 of inner member 312, for example, by welding, and which has a hex cross-section for knob 331 to grip, wherein a thickness between opposing flats of the hex may be approximately 0.094 inch. FIG. 3C illustrates an O-ring type seal 37 fitted between tubular member proximal portion 341 and inner member shaft 301, just distal to interface 31, according to some exemplary embodiments. FIG. 3D, which is a longitudinal cross section through a distal-most segment 34 of tubular member 314 (FIG. 3B) and the corresponding segment of inner member 312, shows inner member boring tip 302, according to an exemplary embodiment, also formed by a separate component, wherein a shank 35 thereof is fitted around and coupled to shaft component 301, for example, by welding.

Figure 4A:
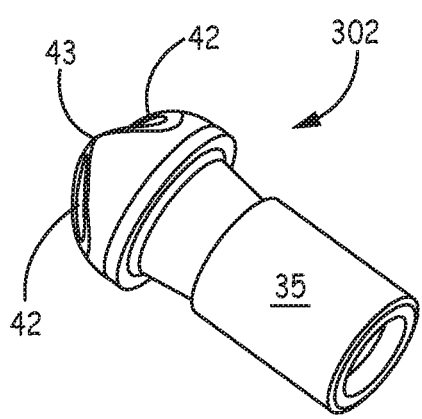
FIG. 4A is a perspective view of an example boring tip of a tunneling assembly.
Figure 4B:
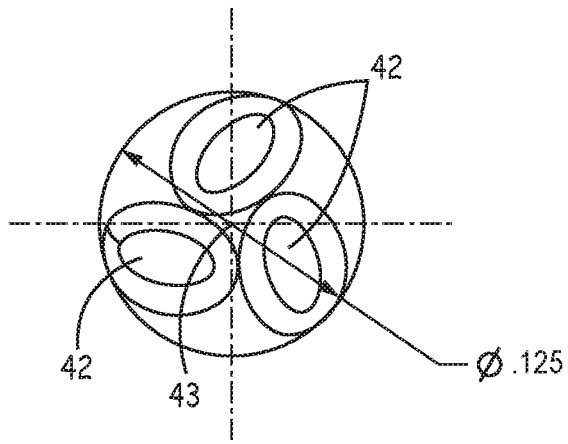
FIG. 4B is an end view of the example boring tip of a tunneling tool.
Figure 5:
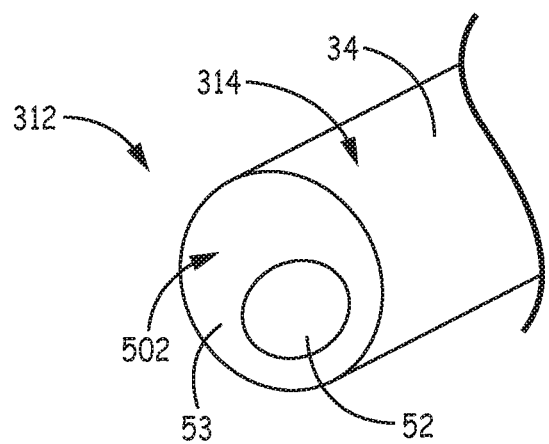
FIG. 5 is a perspective view of another example boring tip.

FIG. 3D further illustrates boring tip 302 including at least one surface 42 recessed from a dome shape (dashed lines) to which tip 302 generally conforms, the at least one surface 42 being offset from a summit of the dome shape that coincides with a distal-most edge 43 of tip 302. According to embodiments of the present disclosure, boring tip 302 of inner member 312 has a blunt configuration, without any sharp edges, so that tip 302 is atraumatic to the patient, when tip 302 is pushed against bodily tissue without being rotated, yet, when rotated, tip 302 will effectively pierce through diaphragmatic attachments 18. FIGS. 4A-B are a perspective view and an end view of tip 302, according to some exemplary embodiments, wherein the at least one surface 42 includes three surfaces 42, each of which has a concave curvature and an elliptical perimeter. FIG. 5 is a perspective view of another boring tip 502 for inner member 312, according to some alternate embodiments. FIG. 5 illustrates tip 502 including at least one surface 52 recessed from the dome shape to which tip 502 generally conforms, similar to tip 302, wherein surface 52 is offset from a distal-most edge 53 of tip 502 (coinciding with the summit of the dome shape), and is relatively flat with a circular perimeter.

With further reference to FIGS. 3A-B, distal-most segment 34 of distal portion 342 of tubular member 314 is shown extending at an angle β relative to tubular member proximal portion 341 and inner member proximal portion 321, wherein angle β may be between approximately 10 degrees and approximately 30 degrees, for example, approximately 15 degrees. FIG. 3B shows tubular member proximal portion 341 including a flat 304, which may serve as an orientation guide when attaching tunneling assembly 310 to handle 330 by inserting tunneling assembly 310 into channel 388 of handle 330. The proper orientation of flat 304 assures that boring tip 302 is oriented generally toward a longitudinally extending alignment horn 337 of handle 330, as shown in FIG. 3A. With reference to FIG. 6, according to some embodiments described in greater detail below, flat 304 interfaces with a block 636 of a lock-and-release mechanism of handle 330. Tubular member 314 may further include a marker 340 that provides an indicator that tunneling assembly 310 is fully inserted within channel 338 of handle 330.

FIG. 3A and FIG. 6, which is a plan view of tool 300 with a portion of a shell 303 of tool handle 330 removed, show horn 337 spaced laterally apart from tunneling assembly 310, and extending parallel to, and coplanar with tubular member distal portion 342. FIG. 6 further illustrates horn 337 including a radiopaque coil 67 mounted and extending longitudinally therein for fluoroscopic monitoring in conjunction with tunneling assembly 310 during the tunneling procedure. FIG. 3A further illustrates horn 337 having a relatively flat profile, for example, having a thickness t that is significantly less than a width w. Handle alignment horn 337 provides some guidance to an operator in approaching and crossing diaphragmatic attachments 18, and in creating a sub-sternal tunnel, as described below in conjunction with FIGS. 7A-B.

FIG. 7A is a schematic showing tool 300 with tunneling assembly boring tip 302/502 having been passed through an incision site IS and positioned against diaphragmatic attachments 18, in proximity to xiphoid process 20. According to some methods, the operator, having gripped around looped gripping portion 332 of handle 330, with thumb and forefinger positioned to engage with knob 331, crosses diaphragmatic attachments 18 with tunneling assembly 310, by spinning knob 331, to cause the positioned boring tip 302/502 to rotate, while pushing tunneling assembly in the superior direction, per arrow SUP. Once across diaphragmatic attachments 18, the operator stops rotating boring tip 302/502, and continues to advance tunneling assembly 310 in the superior direction beneath sternum 13, for example, still gripping around looped gripping portion 332 of handle 330 and also gripping, with another hand, around tubular member 342 in proximity to handle 330, to create a sub-sternal tunnel in which to place a medical device, for example, lead 16 (FIGS. 1A-B).

Figure 7B:
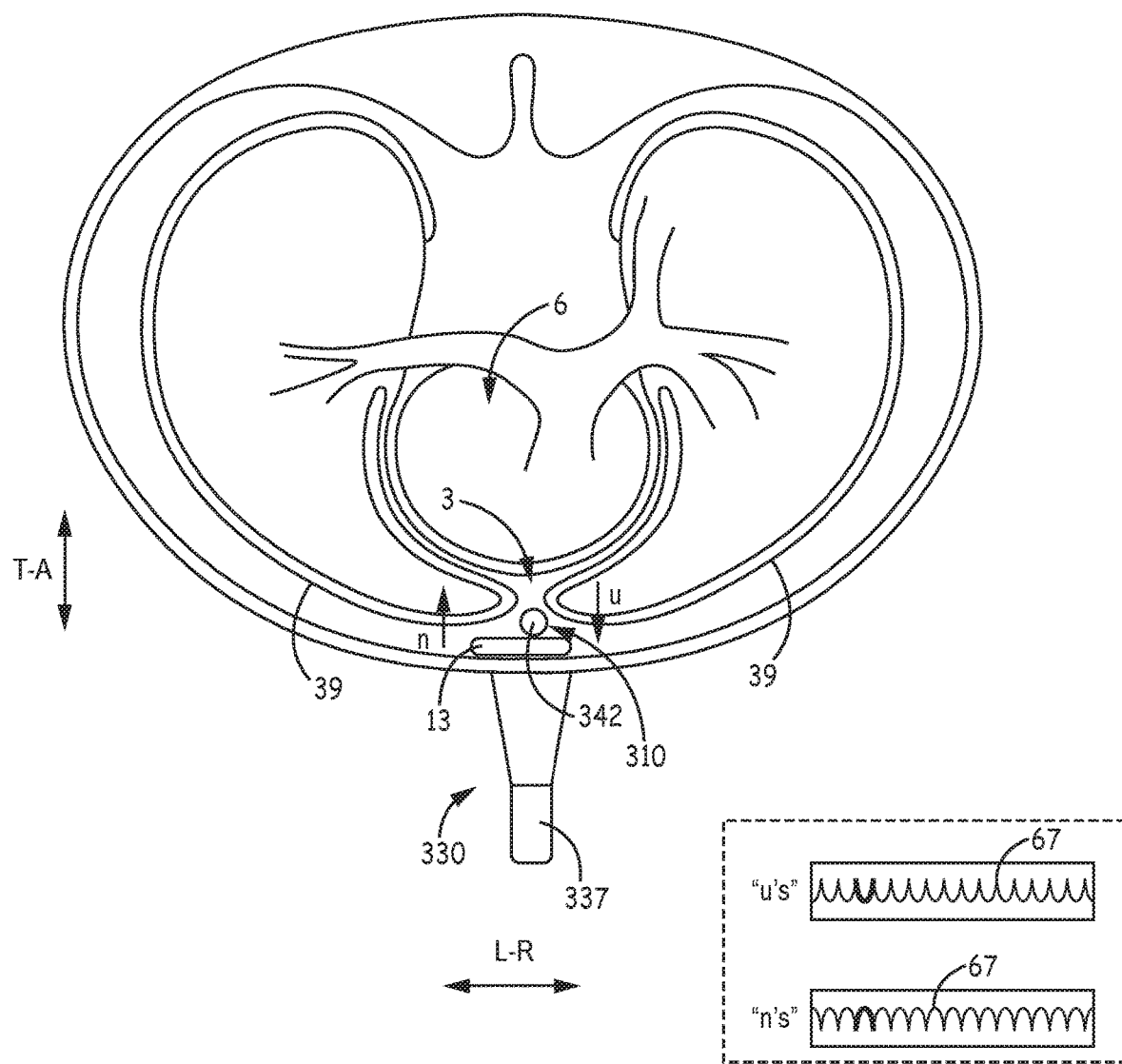
FIG. 7B is a section view along a horizontal plane of the patient, the parallel and coplanar extent of horn and tubular member distal portion provides a visual cue that can help the operator keep tunneling assembly aligned with sternum while advancing the assembly.

The above-described angled distal-most segment 34 of tunneling assembly 310 can keep boring tip 302/502 from being advanced too deep, and with reference to FIG. 7B, which is a section view along a horizontal plane of the patient, the parallel and coplanar extent of horn 337 and tubular member distal portion 342 provides a visual cue that can help the operator keep tunneling assembly 310 aligned with sternum 13 while advancing the assembly 310. Furthermore, the aforementioned relatively flat profile of horn 337 can provide a visual cue to keep the operator from inadvertently rotating tunneling assembly to the patient's left or right, which could point tip 302/502 laterally away from the superior direction of advancement.

According to some preferred methods, the operator fluoroscopically monitors radiopaque coil 67 of horn 337, and tunneling assembly 310 during the tunneling procedure. With further reference to FIG. 7B, the exemplary fluoroscopic images of coil 67 (within the dashed-line box) illustrate a benefit of coil 67 in allowing the operator to use a single fluoroscopic view for guidance, for example, just the AP view, rather than both the AP view and the Lateral view. The AP view enables the operator to detect a heading of tunneling assembly 310 to the patient's left or right (indicated by double-headed arrow L-R), while the contour of the fluoroscopic image of coil 67, either in a string of "u's" or in a string of "n's", gives the operator an indication of whether tunneling assembly 310 is headed toward sternum 13, per arrow u, or away from sternum, per arrow n. It should be noted that the AP view would typically be oriented with the patient's head at the top of the screen, so that the exemplary fluoroscopic images of coil 67 would be rotated 90 degrees. Conversely the Lateral view enables the operator to detect a heading of tunneling assembly 310 either toward or away from the patients sternum 13 (indicated by double-headed arrow T-A), while the contour of the fluoroscopic image of coil 67 gives the operator an indication of the left-right heading of tunneling assembly 310. Methods for fluoroscopic monitoring of radiopaque coil orientation is described in greater detail in the co-pending and commonly assigned United States Patent Application entitled GUIDANCE SYSTEM FOR LOCALIZATION AND CANNULATION OF THE CORONARY SINUS, and having the Ser. No. 14/261,990, which is hereby incorporated by reference in its entirety.

Once the operator has created the sub-sternal tunnel, an introducer sheath (not shown) may be used to position the medical device within the tunnel, for example, by passing the sheath over tunneling assembly 310 and into the tunnel before withdrawing tunneling assembly 310 from the tunnel. According to some embodiments and methods, for example, if handle 330 and tunneling assembly 310 are not separable, an introducer sheath may be pre-loaded around tunneling assembly 310, just distal to handle 330, so that the sheath can be advanced over tunneling assembly 310 and into the tunnel. In these embodiments, the sheath needs to be short enough and tubular member distal portion 342 needs to be long enough so that the pre-loaded sheath does not hinder the tunneling procedure, for example, by inhibiting the operator from gripping directly around tunneling assembly outer member 314 in proximity to handle 330 during the tunneling procedure.

According to some embodiments and methods, handle 330 is detachable from tunneling assembly 310 to allow passage of the introducer sheath over tunneling assembly 310 and into the tunnel, so that the sheath does not need to be pre-loaded. With reference back to FIG. 3A, handle 330 includes the aforementioned lock-and-release mechanism operable via a lever 336, which, when lifted, or rotated, per arrow U, allows the operator to slide tunneling assembly 310 out from channel 338 of handle 330. With further reference to FIG. 3A, the illustrated length of inner member proximal portion 321, which extends proximally from handle 330, can increase the ease of handling tunneling assembly 310, after handle 330 is detached and while passing the introducer sheath thereover.

According to an exemplary embodiment, which is illustrated in FIG. 6, the lock-and-release mechanism of handle 330 includes block 636 mounted within handle shell 303 and coupled to lever 336 via a dowel 606. According to the illustrated embodiment, block 636 defines a portion 338B of channel 338, which, when offset from, or misaligned with, another portion 338A of channel 338 that is defined by handle shell 303, locks tunneling assembly 310 in channel 338, as shown in FIGS. 3A and 6; but, when lever 336 is rotated per arrow U, block is moved, per arrow R, to align channel portions 338A, 338B and thereby release tunneling assembly 310 to slide out from channel 338. According to an exemplary embodiment, lever 336 is formed from polycarbonate, and block 636 from stainless steel, PEI Ultem™ or PEEK.

Figure 8:
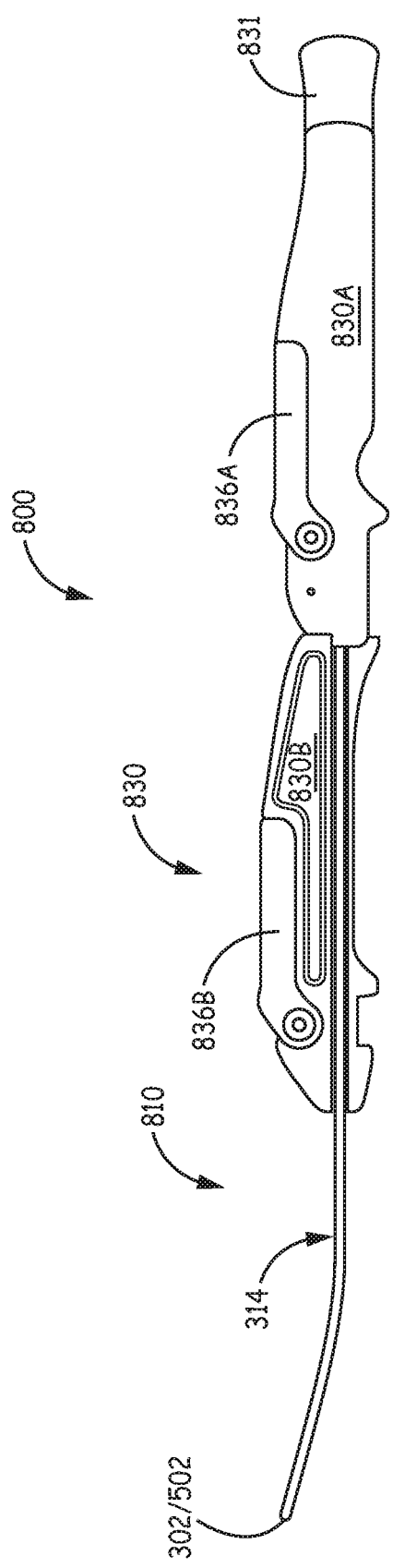
FIG. 8 is a plan view of another example tool according to some alternate embodiments.

FIG. 8 is a plan view of a tool 800, according to some alternate embodiments. FIG. 8 illustrates tool 800 including a tunneling assembly 810, which is similar to tunneling assembly 310, and a two-part handle 830, which has a proximal part 830A and a distal part 830B. With reference back to FIGS. 3B-D, FIGS. 4A-B and FIG. 5, tunneling assembly 810 includes tubular member 314 and inner member 312 extending therein, as described above, yet, in tunneling assembly 810, interface 31 of inner member 312 is located at a proximal-most end of proximal portion 321 for engagement with a knob 831 of handle proximal part 830A. Knob 831, like knob 331, may be engaged by a thumb and fore-finger of an operator to rotate boring tip 302/502 when crossing diaphragmatic attachments 18. Handle distal part 830B is configured to provide a gripping surface for another hand of the operator, as tip 302/502 is being rotated during the crossing and can help to limit the forward travel of tunneling assembly 810 during the crossing. After crossing diaphragmatic attachments and halting the rotation of tip 302/502, handle distal part 830B may be removed from tunneling assembly 810, for example, by lifting lever 836B, to allow sub-sternal passage of a greater length of tunneling assembly 810, when the operator pushes tool 800 in the superior direction to create a sub-sternal tunnel. According to some embodiments, handle proximal part 830A may also be detachable from tunneling assembly 810, for example, by lifting lever 836A, so that an introducer sheath can be passed over tunneling assembly 810 and into the sub-sternal tunnel. Each of handle parts 830A, 830B may include a lock-and-release mechanism similar to that described above for tool 300, in conjunction with FIG. 6.

In the foregoing detailed description, the invention has been described with reference to specific embodiments. However, it may be appreciated that various modifications and changes can be made without departing from the scope of the invention as set forth in the appended claims.

The invention claimed is:

1. A detachable handle assembly for a tool having a tunneling assembly, the tool for creating a sub-sternal tunnel in a patient, and the handle assembly comprising:
   a handle having a handle shell;
   a lock-and-release mechanism comprising a movable block mounted within the handle shell and coupled to a lever via a dowel, the lock-and-release mechanism configured to attach the tunneling assembly to the handle, the lock-and-release mechanism being operable to detach the handle from the tunneling assembly; and
   a knob configured to interlock with the tunneling assembly when the handle assembly is coupled with the tunneling assembly, the knob being configured for engagement by fingers of an adult hand to apply a force to rotate a boring tip of the tunneling assembly.

2. The handle assembly of claim 1, further comprising a looped gripping portion extending laterally from the knob.

3. The handle assembly of claim 1, further comprising a longitudinally extending alignment horn spaced laterally apart from the tunneling assembly and extending parallel to, and coplanar with a distal portion of a tubular member of the tunneling assembly when the handle assembly is coupled with the tunneling assembly; wherein each cross-section profile along a length of the horn generally conforms to a rectangular shape, each cross-section being orthogonal to the longitudinal extent of the horn.

4. The handle assembly of claim 3, wherein the horn includes a radiopaque coil mounted therein, the coil extending longitudinally in the horn.

5. The handle assembly of claim 1, wherein the handle shell includes a handle channel, wherein the block defines a portion of the handle channel, wherein the lever is rotatable to align the portion of the handle channel defined by the block to another portion of the handle channel.

6. A method for positioning a medical device beneath a sternum of a patient using a tool having a tunneling assembly and the detachable handle assembly of claim 1, the method comprising: positioning a boring tip of the tunneling assembly against diaphragmatic attachments in proximity to the patient's xiphoid process, the tunneling assembly comprising a tubular member, and an elongate inner member extending within the outer tubular member from a proximal portion thereof to the boring tip, a proximal portion of each of the tubular and inner members being attached to the handle such that a distal portion of the tubular member extends distally from the handle, and the boring tip of the inner member protrudes out from the distal portion of the tubular member;

causing a rotation of the positioned boring tip, while pushing the tunneling assembly in a superior direction to cross through the diaphragmatic attachments, the rotation being actuated by a hand that grasps the handle;

stopping the rotation of the tunneling assembly boring tip after crossing through the diaphragmatic attachments;

advancing the tunneling assembly beneath the patient's sternum to create a tunnel, after crossing through the diaphragmatic attachments, and without causing any rotation of the tunneling assembly boring tip; and positioning the medical device within the tunnel.

7. The method of claim 6, further comprising monitoring an orientation of a radiopaque coil, via fluoroscopy, while advancing the tunneling assembly, the coil being mounted in a longitudinally extending alignment horn of the handle, the horn being spaced laterally apart from the tunneling assembly, and extending parallel to and coplanar with the distal portion of the tubular member of the tunneling assembly, and the coil extending longitudinally in the horn.

8. The method of claim 6, further comprising:

detaching the handle from the tunneling assembly after advancing the tunneling assembly to create the tunnel;

advancing an introducer sheath over the tunneling assembly and into the tunnel;

removing the tunneling assembly from the advanced introducer sheath; and advancing the medical device through the introducer sheath, after removing the tunneling assembly, to position the device in the tunnel.

9. A detachable handle assembly for a tool having a tunneling assembly, the tool for creating a sub-sternal tunnel in a patient, and the handle assembly comprising:

a handle;

means for detaching the handle from the tunneling assembly, wherein the means for detaching the handle assembly from the tunneling assembly comprises a lock-and-release mechanism by which the tunneling assembly is attached to the handle; and a knob configured to interlock with the tunneling assembly when the handle is coupled with the tunneling assembly, the knob being configured for engagement by fingers of an adult hand to apply a force to rotate a boring tip of the tunneling assembly.

10. The handle assembly of claim 9, further comprising a looped gripping portion extending laterally from the knob.

11. The handle assembly of claim 9, further comprising a longitudinally extending alignment horn spaced laterally apart from the tunneling assembly and extending parallel to, and coplanar with a distal portion of a tubular member of the tunneling assembly when the handle assembly is coupled with the tunneling assembly; wherein each cross-section profile along a length of the horn generally conforms to a rectangular shape, each cross-section being orthogonal to the longitudinal extent of the horn.

12. The handle assembly of claim 11, wherein the horn includes a radiopaque coil mounted therein, the coil extending longitudinally in the horn.

13. The handle assembly of claim 9, wherein the handle shell includes a handle channel, wherein the block defines a portion of the handle channel, wherein the lever is rotatable to align the portion of the handle channel defined by the block to another portion of the handle channel.

\* \* \* \* \*